United States Patent [19]

Mischinski

[11] Patent Number: 4,774,944

[45] Date of Patent: Oct. 4, 1988

[54] HOLDER FOR AN ENDOTRACHEAL TUBE

[76] Inventor: Matthew M. Mischinski, 1095 Springdale Rd., Cherry Hill, N.J. 08003

[21] Appl. No.: 944,769

[22] Filed: Dec. 22, 1986

[51] Int. Cl.$^4$ ..................... A61M 16/00; A61M 25/02
[52] U.S. Cl. ........................ 128/207.17; 128/DIG. 26
[58] Field of Search ...................... 128/207.14, 207.17, 128/DIG. 26, 200.26; 604/174, 179; 2/421, 424; 251/7

[56] References Cited

U.S. PATENT DOCUMENTS

| 3,250,130 | 12/1963 | Lozano | 251/7 |
| 3,774,616 | 11/1973 | White et al. | 128/DIG. 26 |
| 3,993,081 | 11/1976 | Cussel | 128/207.14 |
| 4,235,229 | 11/1980 | Ranford et al. | 128/DIG. 26 |
| 4,248,229 | 2/1981 | Miller | 128/DIG. 26 |
| 4,249,529 | 2/1981 | Nestor et al. | 128/207.17 |
| 4,270,529 | 6/1981 | Muto | 128/207.17 |
| 4,392,857 | 7/1983 | Beran | 128/207.17 |

FOREIGN PATENT DOCUMENTS 2386994 12/1978 France ...................... 2/424

Primary Examiner—William E. Kamm
Assistant Examiner—Timothy G. Philips
Attorney, Agent, or Firm—Robert K. Youtie

[57] ABSTRACT

The invention is concerned with an endotracheal tube holder formed of a generally rigid flat bar having a lateral cut-out leaving a reduced flexible neck connecting the remaining bar portions together for relative swinging about an axis through the neck generally perpendicular to the bar, the cut being configured to conformably receive and circumferentially clamp about a received tube, and one side edge of the bar being provided on respective bar portions with a releasably interengageable catch and a latch which automatically snap into interengagement upon relative swinging movement of the bar portions, all without adversely displacing the tube.

7 Claims, 1 Drawing Sheet

U.S. Patent    Oct. 4, 1988    4,774,944
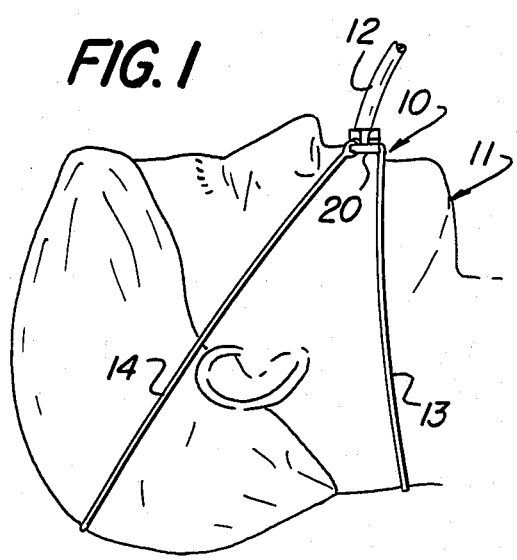
FIG. 1
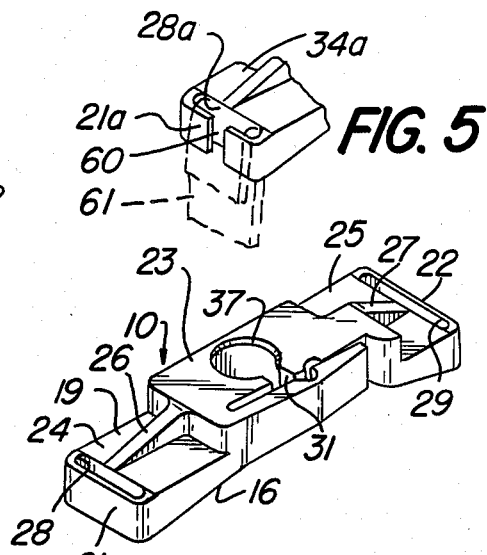
FIG. 5
FIG. 2
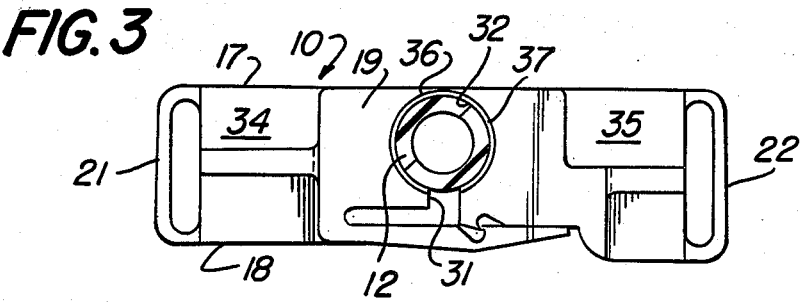
FIG. 3
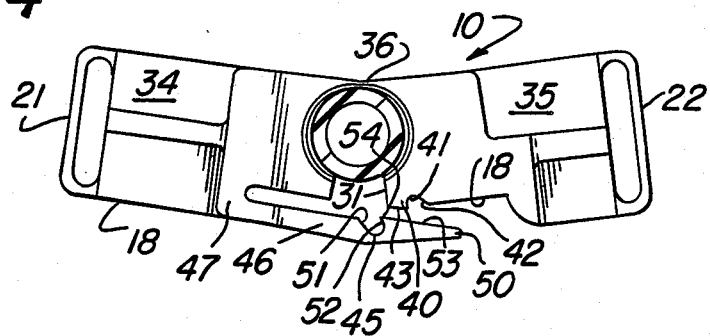
FIG. 4

HOLDER FOR AN ENDOTRACHEAL TUBE

BACKGROUND OF THE INVENTION

In the practice of medicine it is often required that a tube be placed into and held in position in the trachea, usually called an endotracheal tube. It has in the past and continues to be conventional to secure the endotracheal tube by tape wrapped around the tube and applied to the patient's face. This has many disadvantages, including being laborious and time consuming, lacking adjustability, discomfort to the patient, and others. There have been proposed in the prior art endotracheal tube holders intended to eliminate the need for tape, but such devices have introduced other problems. For example, the proposed tube holders have been large and uncomfortable to the patient, permitting possible occlusion of the tube, and otherwise endangering security and safety of the patient's airway.

Applicant is aware of the below listed prior patents:

| U.S. Pat. No. | Date | Patentee |
| --- | --- | --- |
| 4,249,529 | Feb. 10, 1981 | Nestor et al |
| 4,316,459 | Feb. 23, 1982 | Walski |
| 4,351,331 | Sep. 28, 1982 | Gereg |
| 4,378,012 | Mar. 29, 1983 | Brown |
| 4,437,463 | Mar. 20, 1984 | Ackerman |
| 4,449,527 | May 22, 1984 | Hinton |
| 4,483,337 | Nov. 20, 1984 | Clair |
| 4,516,293 | May 14, 1985 | Beran |
| 4,520,813 | June 4, 1985 | Young |
| 4,527,559 | July 9, 1985 | Roxburg et al |
| 4,530,354 | July 23, 1985 | Froilan |
| 4,548,200 | Oct. 22, 1985 | Wapner |

The substantial number of prior art patents indicates the persistence of the problem. Certain of the prior patents require the wrapping of straps around the tube and the patient's head, as in Wapner, U.S. Pat. No. 4,548,200; Roxburg et al, U.S. Pat. No. 4,527,559 and Ackerman, U.S. Pat. No. 4,437,463. The patent to Hinton, U.S. Pat. No. 4,449,527 requires a screw clamp for the tube, while rachet-type bands about the tube are shown in the patents to Beran, U.S. Pat. No. 4,516,293 and Brown, U S. Pat. No. 4,378,012.

The patent to Nestor et al, U.S. Pat. No. 4,249,529 shows a snap engageable clip about the tube, but requires lateral movement of the tube to close and open the clip, very discomforting and possibly dangerous to the patient.

SUMMARY OF THE INVENTION

Accordingly, it is an important object of the present invention to provide an endotracheal tube holder which overcomes the difficulties in the prior art, completely avoids the need for adhesive tape, affords infinite longitudinal adjustability of the tube relative to the holder, is easily sterilizable for sanitation, quickly and easily provides a secure grip on the tube while permitting convenient repositioning or adjustment as desired, is relatively small for comfort to the patient without obstructing access, and is capable of economic mass production for sale at a reasonable price economically justifying single usage and disposal.

Other objects of the present invention will become apparent upon reading the following specification and referring to the accompanying drawings, which form a material part of this disclosure.

The invention accordingly consists in the features of construction, combinations of elements, and arrangements of parts, which will be exemplified in the construction hereinafter described, and of which the scope will be indicated by the appended claims.

BRIEF DESCRIPTION OF THE DRAWINGS

FIG. 1 is a side elevational view showing the invention in operative association with a patient in supine position.

FIG. 2 is a top perspective view of the tube holder of the present invention apart from the tube, straps and patient of FIG. 1.

FIG. 3 is a top plan view of the tube holder illustrated in gripping relation with a tube.

FIG. 4 is a top plan view showing the tube holder in released relation with respect to a tube.

FIG. 5 is a partial perspective view similar to FIG. 2, showing a slightly modified embodiment of end connection.

DESCRIPTION OF THE PREFERRED EMBODIMENTS

Referring now more particularly to the drawings, and specifically to FIG. 1 thereof, there is shown a tube holder 10 on the mouth of a patient 11 holding in position an endotrachael tube 12. The endotracheal tube 12 is shown in FIG. 1 passing through the holder 10, and the holder is held in position on the patient 11 by suitable head straps as as 13 and 14.

The endotracheal tube holder 10 is best seen in integrally of plastic, or other suitable material, as by injection molding, or otherwise, as desired. The holder may, overall, be considered a bar-like, plate or body 16, generally elongate longitudinally between laterally spaced side edges 17 and 18, and of a thickness or depth between the front or top face 19 and under surface 20, so that the bar is substantially rigid or stiff.

The underside of the bar 16 may be arcuate or generally concave in the longitudinal direction, as between opposite ends 21 and 22, for comfortable engagement with the patient's mouth or lips. The longitudinal medial portion of the body 16, on the outer or front side may be raised, as by a boss 23, the bar or plate body 16 being of reduced thickness in the end portions 24 and 25 extending from the thickened central portion 23 outwardly to ends 21 and 22, respectively. Rigid reinforcing ribs 26 and 27 may be provided on the front of respective plate portions 24 and 25, extending longitudinally of the plate and terminating short of the plate ends 21 and 22. Adjacent to respective plate ends 21 and 22 are laterally extending through holes or slots 28 and 29 for receiving the ends of head straps or ties 13 and 14.

The central thickened plate portion 23, on the longitudinal side 18, is formed with a transverse slot 31, extending between and opening through the front and rear of the bar 16. The slot 31 extends laterally inwardly of the body 16 to define an enlarged cut-out or through opening 32 extending toward and terminating short of the opposite side edge 17. The through opening or cut-out 32 may be of generally circular configuration, see FIG. 3, and has its bounding edge of an arcuate angular extent approaching 360°, less the width of slot 31 in the direction longitudinal of the plate. The cut-out or opening terminates adjacent to the plate side edge 17 to subdivide the plate or body 16 into a pair of plate portions 34 and 35 connected together by the intermediate, relatively narrow plate region 36 remaining between the cut-out 32 and side edge 17 of the plate. The remaining plate region 36 connecting the opposite plate end portions 34, 35, is a thickness or dimension laterally of the plate to afford flexibility, as by the nature of the plastic composition, and thereby connect together the plate portions 34, 35 for a hinged or relative swinging movement about an axis generally normal to the plate and through the hinge connection 36.

The reduced hinge portion or neck 36 is molded in the plate 16 so that the plate portions 34 and 35 are normally swung slightly away from each other, the position shown in FIG. 4, when the neck or hinge portion 36 is in an unstressed condition.

The bounding internal edge of the cut-out or opening 32 may advantageously be chamfered or beveled as at 37 on one or both sides of the plate body 16, to facilitate the insertion there through of an endotracheal tube.

On one side edge of the body 16, say side edge 18 opposite to the hinged neck 36, there may be provided a catch or hook 40. The catch or hook 40 is undercut, as at 41, facing toward the adjacent end 22 of the body, as by formation of a notch 42 extending into the side edge 18 adjacent to and spaced from the slot 31. That is, the notch 42 is provided in the plate portion 35; and, the portion of plate edge 18 between slot 31 and notch 42 is defined by a ramp or oblique surface 43 extending longitudinally of the body 16, and diagonally laterally outwardly toward the body end 22. Thus, the catch 40 constitutes a generally hooked shaped formation defined between the ramp 43 and the undercut surface 41 of notch 42.

A latch 45 is also provided on the side edge 18 of body 16, but on the other body portion 34 and is constituted of an elongate arm 46 connected at one end region 47 to the plate portion 34 along side edge 18. The arm connecting region 47 is located in spaced relation between the slot 31 and plate end 21 of plate portion 34. This arm connecting portion 47 mounts the arm 46 for resiliently yieldable swinging movement about the connecting portion.

The latch arm 46 extends to a free end portion 50 which, in the unstressed or relaxed condition of FIG. 4 extends along and laterally outwardly of the catch 40 and terminates beyond the notch 42. More specifically, the latch arm 46 is provided on its inner side, facing toward the slot 31 and catch 40 with a notch or indent 51 which opens or faces obliquely inwardly and generally toward the distal body end 21. By its oblique relation, the notch or indent 51 provides an undercut, interior surface 52, and overlying the undercut surface 52 and facing toward the ramp 43 the latch arm 46 is provided with a cam surface 53. The intersection of the cam surface 53 and the undercut surface 52 provides a catch hook or point 54.

In operation, it is only necessary to relatively rotate the plate portions 34, 35 toward each other from the position of FIG. 4 about the hinge or neck 36, whereupon the cam surface 53 rides on the ramp 43 longitudally outwardly toward the plate end 22 until the latch hook or point 54 snaps past the catch 40 and into the notch 44 for retaining engagement of the undercut surface 41, the condition shown in FIG. 3.

In this closed condition of FIG. 3, the tube 12 is firmly gripped throughout substantially its entire circumference to effectively prevent relative movement between the tube and holder. However, release of the tube may be quickly and easily effected by merely the snapping open of the latch 45, as by a finger pull laterally outwardly on the latch arm end 50. By the generally circular configuration of cut-out 32, the received tube 12 is not kinked or otherwise closed, and a range of tubes may be employed with a single holder, while various sizes of holders may be provided, as desired.

In the embodiment as shown in FIG. 5, the plate portion 34a has its end portion 21a formed with a through, laterally extending slot or strap opening 28a. In addition, an entry slit 60 is provided to the strap receiving slot 28a, as by the slit extending the entire thickness of the plate portion, laterally medially of the slot ends. By this means, a strap 61 shown in phantom, may be moved sideways through the slit 60 and into the slot 28a, without the tedious lengthwise threading of the strap.

An important aspect of this invention resides in the holder 10 enabling the endotracheal tube 12 to be grasped and released without appreciable sideways movement of the tube, to minimize discomfort to the patient. This may be observed in FIGS. 3 and 4, where the tube 12 may remain in its position, while the holder 10 is opened and closed with respect to the tube, without causing lateral movement of the tube.

From the foregoing, it is seen that the present invention provides an endotracheal tube holder which is extremely simple in construction, highly automatic in operation, which minimizes discomfort and possible damage to the patient, and otherwise fully accomplishes its intended object.

Although the present invention has been described in some detail by way of illustration and example for purposes of clarity of understanding, it is understood that certain changes and modifications may be made within the spirit of the invention.

What is claimed is:

1. A holder for an endotracheal tube, said holder being integrally fabricated of plastic and comprising a substantially rigid elongate flat bar, attachment means at opposite ends of said bar for attachment to a head strap, said bar having a slot entering laterally into one side edge at a location spaced between the ends of said bar and opening through opposite faces of said bar, said slot having an enlarged inner region defining a tube receiving cut-out located adjacent to and spaced from the other side edge of said bar to leave a reduced flexible neck opposite to said slot entering location, said bar being subdivided by said cut-out into substantially rigid portions on opposite sides of said cut-out connected by said neck for relative swinging movement of the bar portions toward and away from each other constrained only about an axis through said neck perpendicular to said bar for gripping and releasing a tube without substantial tube movement, a catch on said one side edge of one bar portion, and a latch on said side edge of the other bar portion and releasably interengagable with said catch when the bar portions are swung toward each other.

2. An endotracheal tube holder according to claim 1, said cut-out having its internal surface of substantially circular configuration less than 360° by the width of said slot and substantially equally divided between respective bar portions, for equal clamping engagement of the bar portions with a tube received in said cut-out.

3. An endotracheal tube holder according to claim 1, said catch comprising an undercut facing away from said slot, and said latch comprising an arm extending over said slot and a hook on said arm for retaining engagement with said undercut.

4. An endotracheal tube holder according to claim 3, said catch comprising a ramp facing outwardly from said one bar portion, and said latch arm being resilient and including a cam facing inwardly towards said ramp and riding over the latter and snapping into said releasable interengagement upon relative swinging of said bar portions toward each other.

5. An endotracheal tube holder according to claim 4, said neck being resiliently flexible and assuming in its unstressed condition a position displacing said bar portions partially away from each other for free selective longitudinal displacement of a received tube relative to the holder.

6. An endotracheal tube holder according to claim 4, said ramp being located between said undercut and slot, and said cam being located on said latch arm outwardly beyond said hook, for relative riding of said cam and ramp and snapping into said releasable interengagement.

7. An endotracheal tube holder according to claim 6, said cut-out being beveled on one face of said bar to facilitate endwise tube insertion into said cut-out.

* * * * *